United States Patent
Bouteffah-Touiki et al.

(10) Patent No.: US 10,514,387 B2
(45) Date of Patent: Dec. 24, 2019

(54) METHOD FOR MONITORING THE FUNCTIONALITY OF A WASH STATION FOR PIPETTING NEEDLES

(71) Applicant: Siemens Healthcare Diagnostics Products GmbH, Marburg (DE)

(72) Inventors: Ayoub Bouteffah-Touiki, Frankfurt am Main (DE); Thorsten Michels, Gross-Gerau (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 112 days.

(21) Appl. No.: 15/135,343

(22) Filed: Apr. 21, 2016

(65) Prior Publication Data

US 2016/0313360 A1     Oct. 27, 2016

(30) Foreign Application Priority Data

Apr. 27, 2015   (EP) .................................... 15165186

(51) Int. Cl.
*G01N 35/10*     (2006.01)
(52) U.S. Cl.
CPC .  *G01N 35/1004* (2013.01); *G01N 2035/1025* (2013.01)
(58) Field of Classification Search
USPC ......................................................... 73/1.74
See application file for complete search history.

(56) References Cited

U.S. PATENT DOCUMENTS

| | | | | |
|---|---|---|---|---|
| 4,179,339 A  * | 12/1979 | Sogi | ....................... | C12M 33/04 |
| | | | | 285/192 |
| 4,788,150 A  * | 11/1988 | Nelson | ................... | G01N 35/02 |
| | | | | 324/667 |
| 4,961,906 A  * | 10/1990 | Andersen | ........... | G01N 35/1002 |
| | | | | 422/501 |
| 5,529,754 A  * | 6/1996 | Bonacina | ............... | G01B 7/023 |
| | | | | 324/519 |
| 5,635,043 A  * | 6/1997 | Tur yan | .................. | G01N 27/42 |
| | | | | 204/412 |
| 8,570,029 B2 * | 10/2013 | Andres | ................. | B01L 3/0217 |
| | | | | 324/207.2 |
| 8,721,966 B2 * | 5/2014 | Shibutani | ............... | G01N 35/10 |
| | | | | 422/68.1 |
| 9,421,538 B1 * | 8/2016 | Sung | ....................... | B01L 3/021 |
| 9,678,094 B2 * | 6/2017 | Brade | ................ | G01N 35/1009 |

(Continued)

FOREIGN PATENT DOCUMENTS

| CN | 2588334 Y | 11/2003 |
|---|---|---|
| CN | 104111102 A | 10/2014 |

(Continued)

OTHER PUBLICATIONS

European Search Report of European Application No. 15165186. 6-1553 dated Oct. 9, 2015.

(Continued)

*Primary Examiner* — Natalie Huls
*Assistant Examiner* — Mohammed E Keramet-Amircolai
(74) *Attorney, Agent, or Firm* — Dugan & Dugan, PC

(57) ABSTRACT

The present invention lies in the field of automated analysis devices and relates to a method for monitoring the functionality of a wash station (1) for pipetting needles (2).

17 Claims, 1 Drawing Sheet

(56) References Cited

U.S. PATENT DOCUMENTS

| | | | | |
|---|---|---|---|---|
| 2003/0203491 A1* | 10/2003 | Andrevski | ............ | B01L 3/5025 436/46 |
| 2005/0124059 A1* | 6/2005 | Kureshy | ............ | G01N 35/1011 435/287.2 |
| 2006/0081539 A1* | 4/2006 | Safar | ................. | B01L 3/5082 210/695 |
| 2006/0105359 A1* | 5/2006 | Favuzzi | ................. | B01L 3/508 435/6.19 |
| 2008/0058065 A1* | 3/2008 | Okada | ................. | G07F 17/32 463/20 |
| 2008/0228163 A1* | 9/2008 | Smith | ................ | B01L 3/50825 604/411 |
| 2011/0127292 A1* | 6/2011 | Sarofim | ................. | B01L 9/52 422/521 |
| 2012/0156796 A1* | 6/2012 | Drechsler | ............ | G01N 21/03 436/164 |
| 2013/0195718 A1* | 8/2013 | Michels | ................. | B01L 3/021 422/63 |
| 2014/0186234 A1* | 7/2014 | Maruyama | ......... | G01N 35/1004 422/510 |
| 2014/0193300 A1* | 7/2014 | Bernhard | ............... | G01N 35/04 422/64 |
| 2014/0271403 A1* | 9/2014 | Wilmes | ............... | G01N 35/025 422/509 |
| 2014/0271405 A1* | 9/2014 | Wilmes | ............. | G01N 35/1079 422/511 |
| 2015/0275162 A1* | 10/2015 | Saito | ..................... | C12M 21/18 435/293.1 |
| 2015/0323776 A1* | 11/2015 | Dyson-Holland | ..... | G01N 1/312 348/79 |
| 2016/0061644 A1 | 3/2016 | Ma et al. | | |
| 2017/0097289 A1* | 4/2017 | Barnett | ................ | G01N 1/312 |

FOREIGN PATENT DOCUMENTS

| | | |
|---|---|---|
| WO | WO97/03766 | 2/1997 |
| WO | WO 2014/175018 | 10/2014 |

OTHER PUBLICATIONS

Chinese Search Report of Chinese Application No. 2016101819086 dated Mar. 18, 2019.

\* cited by examiner

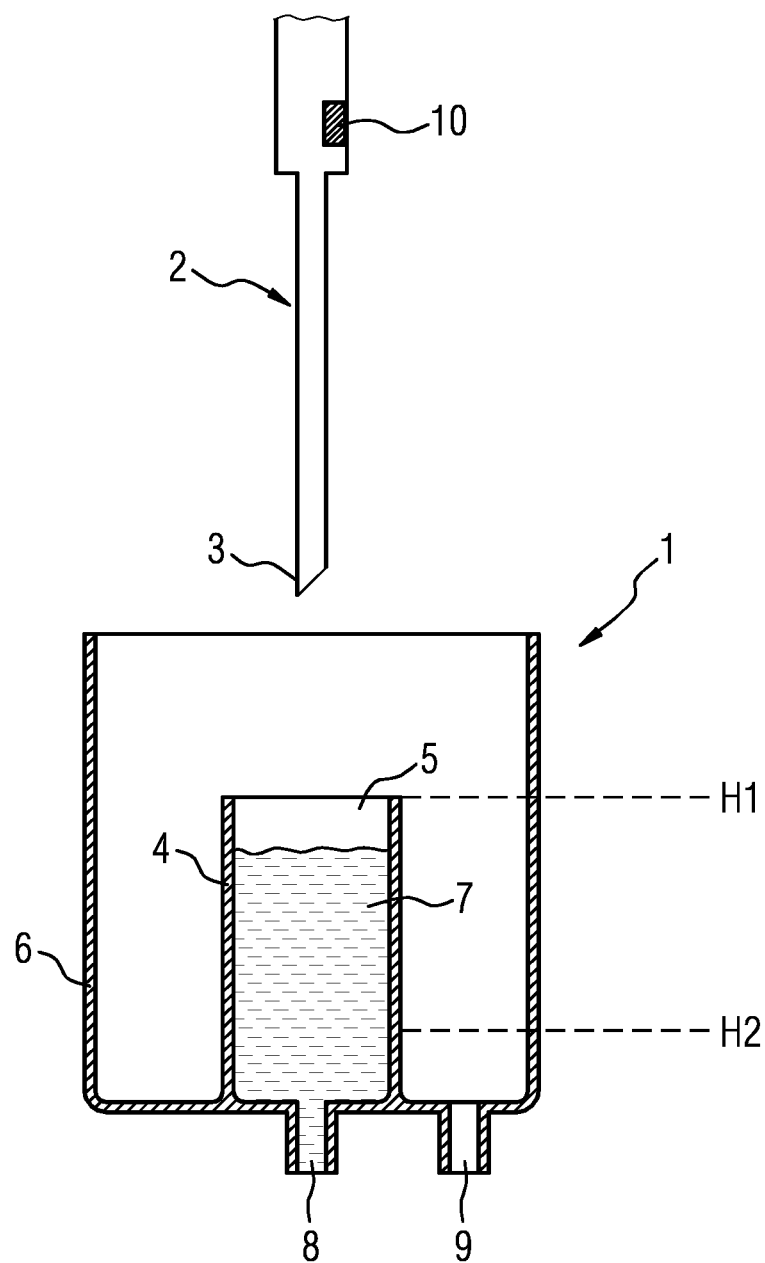

METHOD FOR MONITORING THE FUNCTIONALITY OF A WASH STATION FOR PIPETTING NEEDLES

CROSS REFERENCE TO RELATED APPLICATION

This claims priority to European Patent Application No. EP 15165186.6, filed Apr. 27, 2015, which is hereby incorporated by reference herein in its entirety for all purposes.

FIELD

The present invention lies in the field of automated analysis devices and relates to a method for monitoring the functionality of a wash station for pipetting needles.

BACKGROUND

Current analysis devices, as are routinely used in analytics, forensics, microbiology and clinical diagnostics, are able to carry out a multiplicity of detection reactions and analyses with a multiplicity of samples. In order to be able to carry out a multiplicity of examinations in an automated manner, various automatically operating apparatuses for the spatial transfer of measurement cells, reaction containers and reagent liquid containers are required, such as, e.g., transfer arms with gripper functions, transport belts or rotatable transport wheels, as well as apparatuses for transferring liquids, such as, e.g., pipetting apparatuses. The devices comprise a central control unit which, by means of appropriate software, is able to largely autonomously plan and work through the work steps for the desired analyses.

Many of the analysis methods used in such analysis devices operating in an automated manner are based on optical methods. Measurement systems based on photometric (e.g. turbidimetric, nephelometric, fluorometric or luminometric) or radiometric measurement principles are particularly widespread. These methods enable the qualitative and quantitative detection of analytes in liquid samples without having to provide additional separation steps. The determination of clinically relevant parameters, such as, e.g., the concentration or the activity of an analyte, is often implemented by virtue of an aliquot of a bodily fluid of a patient being mixed simultaneously or in succession with one or more test reagents in a reaction vessel, as a result of which a biochemical reaction is put into motion, which brings about a measurable change in an optical property of the test preparation.

The measurement result is, in turn, forwarded into a storage unit by the measurement system and evaluated. Subsequently, the analysis device supplies a user with sample-specific measurement values by way of an output medium, such as, e.g., a monitor, a printer or a network connection.

Sample liquids or reagent liquids are usually transferred by means of automated pipetting apparatuses. Such pipetting apparatuses generally comprise a height-adjustable pipetting needle arranged vertically on a displaceable transfer arm, which pipetting needle is connected to a pumping unit such that a desired volume of liquid can be taken from a container by way of the pipetting needle, and output into a target container at a different location. Usually, the pipetting needle is displaced to a position over a liquid container with the aid of the transfer arm and then lowered into the liquid container and into the liquid contained therein. Once the desired volume has been withdrawn, the pipetting needle is driven upward and then driven to the desired target position over a liquid container, e.g., over a measurement cell, with the aid of the horizontally displaceable transfer arm. There, the pipetting needle is lowered again, and the amount of liquid is output.

It is conventional to equip pipetting apparatuses with a fill-level sensor. The purpose of this is, firstly, to be able to determine the fill level of reagent liquids in reagent liquid containers during the operation of the automated analysis device and report this to the control unit. What this ensures, for example, is that a user can be informed in good time about a necessary reagent container replacement. Secondly, determining the fill level ensures that the pipetting needle is always immersed sufficiently deeply into the liquid to be withdrawn in order to avoid air being suctioned-in in place of liquid.

The most common method for determining the fill level is the determination of the fill level by capacitive means. To this end, the pipetting needle consists of an electrically conductive material and hence, in principle, forms the measurement electrode, and it furthermore comprises a reference electrode. The fill level can be determined continuously from the change in the electric capacitance between the pipetting needle and the reference electrode. Determining the fill level by optical means is another method. To this end, the pipetting needle comprises an optoelectronic fill-level sensor consisting of a light source and a light sensor. In the case of immersion, the light is refracted by the liquid and it no longer reaches the light sensor, or it only reaches the latter in attenuated form. The fill level can be determined from the attenuation of the light signal.

The pipetting needle tips must be cleaned after each instance of pipetting sample or reagent liquid before they can be used for the processing of further reagents or samples. In an analysis device, special wash stations are provided for cleaning pipetting needle tips. Conventional wash stations are composed of an inner wash fountain cylinder, which is filled or fillable with a wash liquid, and an outer overflow cylinder. For cleaning purposes, the pipetting needle tip is lowered into the wash fountain cylinder and immersed into the wash liquid. In some systems, the wash liquid is sprayed into the wash fountain cylinder with a high flow velocity through nozzles in order to optimize the cleaning process. In some systems, wash liquid is suctioned-in and emitted again so that the interior of the pipetting needle tip is cleaned as well. In other systems, the pump apparatus of the pipetting apparatus comprises a direct supply of wash liquid such that the wash liquid is pumped through the whole pipetting needle and subsequently emitted into the wash fountain cylinder. The outer overflow cylinder surrounding the wash fountain cylinder is provided to collect wash liquid which passes over the edge of the wash fountain cylinder. A drain is usually provided in the overflow cylinder, by means of which the collected wash liquid can flow out of the wash station or can be suctioned therefrom. By way of example, such a wash station for a pipetting needle is described in WO-A1-97/03766.

A problem is that, for example, the drain can be blocked, as a result of which—in the worst case—the wash station overflows and wash liquid can reach into the analysis device and cause major damage as a result thereof. Other malfunctions, such as, e.g., uncontrolled filling with wash liquid or a failure of a suctioning apparatus, can also cause an overflow of a wash station.

It is therefore necessary to adopt measures which identify and indicate the risk of the overflow of a wash station in good time.

SUMMARY

The object underlying the present invention is therefore that of providing a method which enables the monitoring of the functionality of a wash station for pipetting needles in an automated analysis device.

This object is achieved by virtue of the fill level of the wash liquid being measured with the aid of the fill-level sensor when lowering a pipetting needle into the wash station.

This is advantageous in that an overflow of the wash station is identified in good time and measures can be adopted to avoid impending damage to the analysis device. What is particularly advantageous is that the method can be carried out in any analysis device which already comprises a pipetting apparatus with a fill-level sensor, without carrying out structural modifications of the analysis device. All that is required is to configure the control unit in such a way that the fill level is also measured in the wash station and evaluated accordingly. It is possible to dispense with an application of a fill-level sensor on the wash station itself.

The subject matter of the present invention is therefore the novel use of a pipetting needle with a fill-level sensor for monitoring the functionality of a wash station for a pipetting needle in an automated analysis device.

The invention relates to a method for monitoring the functionality of a wash station for a pipetting needle in an automated analysis device, wherein the wash station has an inner wash fountain cylinder filled with a wash liquid, with an opening for receiving a pipetting needle tip, and an outer overflow cylinder, which surrounds the wash fountain cylinder and exceeds the height of the latter, and wherein the pipetting needle has a fill-level sensor. The method comprises the following steps:

a. lowering the pipetting needle such that the pipetting needle tip is introduced into the wash fountain cylinder;

b. measuring the fill level of the wash liquid in the wash station by means of the fill-level sensor; and c. comparing the measured fill level with a first threshold, which corresponds to the height of the wash fountain cylinder.

If a fill level which lies above the first threshold is measured in this way, this means that so much wash liquid has already collected in the overflow cylinder that there is a risk of the wash station overflowing in the case of a further supply of wash liquid.

Therefore, preferably, an error report is generated and/or the supply of wash liquid into the wash fountain cylinder is stopped if the measured fill level lies above the first threshold.

The error report serves to inform a user of the automated analysis device about the malfunction of the wash station. This enables the adoption of required measures for lifting the malfunction by the user in good time.

The error report can be indicated on a screen of the automated analysis device in the form of a text message or in the form of a pictogram. Alternatively or additionally, the error report can also be output in the form of an acoustic signal by a loudspeaker of the automated analysis device. Moreover, the error report can also be output in the form of a visual signal by a warning lamp of the automated analysis device. Naturally, the various options for reporting an error can be combined with one another as desired.

The supply of wash liquid into the wash fountain cylinder is preferably stopped automatically. To this end, if the measured fill level lies above the first threshold, an appropriate control signal is transmitted from the control unit to the apparatus, such as e.g. a pump, which fills the wash station with wash liquid.

In a preferred embodiment of the method according to the invention, the measured fill level is compared with a second threshold, which corresponds to a minimum required fill level of the wash liquid in the wash fountain cylinder.

If a fill level which lies below the second threshold is measured in this way, this means that there is not a sufficient amount of wash liquid in the wash cylinder to ensure sufficient cleaning of the pipetting needle tip.

Accordingly, the second threshold is selected in such a way that it lies below the height of the wash fountain cylinder but that it specifies a minimum height of the fill level of the wash liquid in the wash fountain cylinder, which is required for sufficient cleaning of the pipetting needle tip.

Therefore, preferably, an error report is generated and/or the use of the pipetting needle for pipetting reagent and/or sample liquid is stopped if the measured fill level lies below the second threshold.

The error report can be indicated or output in various ways, as already described further above.

Preferably, the use of the pipetting needle for pipetting reagent and/or sample liquid is stopped automatically. To this end, if the measured fill level lies below the second threshold, the control unit transmits an appropriate control signal to, e.g., the automatically displaceable transfer arm, to which the pipetting needle is attached, and each further movement of the transfer arm, and hence of the pipetting needle, is prevented.

In a preferred embodiment of the method according to the invention, the fill level of the detergent in the wash station is measured by capacitive means. To this end, the pipetting needle has a capacitive fill-level sensor. Preferably, the pipetting needle, to this end, consists of an electrically conductive material, such as, e.g., stainless steel, and therefore, in principle, forms the measurement electrode, and it furthermore comprises a reference electrode.

Alternatively, the fill level of the detergent in the wash station can also be measured optically. To this end, the pipetting needle has an optoelectronic fill-level sensor, which comprises at least a light source and a light sensor. Furthermore, every measurement method, in which the fill-level sensor is arranged on the pipetting apparatus or on the pipetting needle and is displaceable therewith in the analysis device, is suitable.

A further subject matter of the present invention relates to an automated analysis device with at least one automatically displaceable pipetting apparatus, which comprises a pipetting needle with a fill-level sensor, and with at least one wash station for the pipetting needle, wherein the wash station has an inner wash fountain cylinder filled with a wash liquid, with an opening for receiving a pipetting needle tip, and an outer overflow cylinder, which surrounds the wash fountain cylinder and exceeds the height of the latter. The analysis device according to the invention furthermore has a controller, which is configured in such a way that it controls a method with the following steps:

a. lowering the pipetting needle such that the pipetting needle tip is introduced into the wash fountain cylinder;

b. measuring the fill level of the wash liquid in the wash station by means of the fill-level sensor; and c. comparing the measured fill level with a first threshold, which corresponds to the height of the wash fountain cylinder.

Preferably, the controller is furthermore configured in such a way that an error report is generated and/or the supply of wash liquid into the wash fountain cylinder is stopped if the measured fill level lies above the first threshold.

In a preferred embodiment of the analysis device according to the invention, the controller is furthermore configured in such a way that the method controlled thereby furthermore comprises the following step: comparing the measured fill level with a second threshold, which corresponds to a minimum required fill level of the wash liquid in the wash fountain cylinder.

Preferably, the controller is furthermore configured in such a way that an error report is generated and/or the use of the pipetting needle for pipetting reagent and/or sample liquid is stopped if the measured fill level lies below the second threshold.

Preferably, the controller is furthermore configured in such a way that an error report is indicated on a screen of the automated analysis device in the form of a text message or in the form of a pictogram, or is output in the form of an acoustic signal by a loudspeaker of the automated analysis device or output in the form of a visual signal by a warning lamp of the automated analysis device.

In a preferred embodiment of the analysis device according to the invention, the fill-level sensor connected to the pipetting needle is a capacitive fill-level sensor.

Preferably, to this end, the pipetting needle consists of an electrically conductive material, such as, e.g., stainless steel, and furthermore comprises an electrode.

Alternatively, the fill-level sensor connected to the pipetting needle can also be an optoelectronic fill-level sensor which comprises at least a light source and a light sensor.

BRIEF DESCRIPTION OF THE DRAWINGS

The invention will be explained on the basis of a drawing.

Persons skilled in the art will understand that the drawings, described below, are for illustrative purposes only. The drawings are not necessarily drawn to scale and are not intended to limit the scope of this disclosure in any way.

FIG. 1 shows a wash station 1 for a pipetting needle 2 in an analysis device not depicted in any more detail.

DETAILED DESCRIPTION

The wash station 1 comprises an inner wash fountain cylinder 4 which is almost completely filled with a wash liquid 7 and which has an opening 5 for receiving a pipetting needle tip 3, and an outer overflow cylinder 6, which surrounds the wash fountain cylinder 4 and exceeds the height of the latter. The wash liquid 7 is pumped from a reservoir (not depicted here) into the wash fountain cylinder 4 by way of a supply opening 8. In the embodiment shown here, provision is made for a continual replacement of wash liquid 7 to take place by virtue of fresh wash liquid 7 being pumped into the wash fountain cylinder 4 from below, while excess wash liquid 7 passes over the edge of the wash fountain cylinder 4 and into the overflow cylinder 6. The used wash liquid 7 is pumped away from the wash station 1 by way of a drainage opening 9 in the overflow cylinder 6.

The pipetting needle 2 has a capacitive fill-level sensor. To this end, the pipetting needle 2 consists of stainless steel and therefore serves as a measurement electrode, and it furthermore comprises a reference electrode 10. If the pipetting needle 2 is situated in the air, a low capacitance is measured. When the pipetting needle tip 3 is immersed into the wash liquid 7, a change in the capacitance is measured. The fill level of the wash liquid 7 is calculated from the lowering path of the pipetting needle 2 to the point with the change in capacitance.

For the purposes of cleaning the pipetting needle tip 3, the pipetting needle 2 is lowered over the wash fountain cylinder 4 to such an extent that the pipetting needle tip 3 is immersed so deep into the wash liquid 7 as is at least required for a sufficiently thorough clean. In the embodiment shown here, a minimum fill-level height is provided, which is set by a threshold H2. If the fill-level sensor detects a fill-level height lying below the threshold H2, this means that there is not a sufficient amount of wash liquid 7 in the wash fountain cylinder 4, and so sufficient cleaning of the pipetting needle tip 3 is not ensured.

Furthermore, a maximum fill-level height, which is set by a threshold H1, is provided in the embodiment shown here. The threshold H1 corresponds to the height of the wash fountain cylinder 4. If the fill-level sensor detects a fill-level height lying above the threshold H1, this means that so much wash liquid 7 has already collected in the overflow cylinder 6 that, in the case of a further supply of wash liquid 7, there is a risk of the wash station 1 overflowing.

LIST OF REFERENCE SIGNS

1 Wash station
2 Pipetting needle
3 Pipetting needle tip
4 Wash fountain cylinder
5 Opening
6 Overflow cylinder
7 Wash liquid
8 Supply opening
9 Drainage opening
10 Reference electrode
H1 First threshold for a maximum fill-level height
H2 Second threshold for a minimum fill-level height

What is claimed is:

1. A method for monitoring the functionality of a wash station for a pipetting needle in an automated analysis device, wherein the wash station has an inner wash fountain cylinder filled with a wash liquid, with an opening for receiving a pipetting needle tip, and an outer overflow cylinder, which surrounds the wash fountain cylinder and exceeds the height of the latter, and wherein the pipetting needle has a fill-level sensor, the method comprising the following steps:

lowering the pipetting needle such that the pipetting needle tip is introduced into the wash fountain cylinder;
   measuring the fill level of the wash liquid in the wash station with the fill-level sensor; and
   comparing the measured fill level with a first threshold, which corresponds to the height of the wash fountain cylinder.

2. The method as claimed in claim 1, wherein an error report is generated if the measured fill level lies above the first threshold.

3. The method as claimed in claim 1, further comprising the following step:
   stopping the supply of wash liquid into the wash fountain cylinder.

4. The method as claimed in claim 1, further comprising the following step:

comparing the measured fill level with a second threshold, which corresponds to a minimum required fill level of the wash liquid in the wash fountain cylinder.

5. The method as claimed in claim 4, wherein an error report is generated if the measured fill level lies below the second threshold.

6. The method as claimed in claim 2, wherein the error report is indicated on a screen of the automated analysis device in the form of a text message or in the form of a pictogram, or is output in the form of an acoustic signal by a loudspeaker of the automated analysis device or output in the form of a visual signal by a warning lamp of the automated analysis device.

7. The method as claimed in claim 1, wherein the pipetting needle has a capacitive fill-level sensor and the fill level is measured by capacitive means.

8. The method as claimed in claim 1, wherein the measuring comprises:
   measuring a measurement parameter with the fill level sensor as the pipetting needle moves toward the wash liquid until a measured value of the measurement parameter changes; and
   calculating the fill level based on the lowering path of the pipetting needle which ends at a point at which the measured value of the measurement parameter changes.

9. An automated analysis device with at least one automatically displaceable pipetting apparatus, which comprises a pipetting needle with a fill-level sensor, and with at least one wash station for the pipetting needle, wherein the wash station has an inner wash fountain cylinder filled with a wash liquid, with an opening for receiving a pipetting needle tip, and an outer overflow cylinder, which surrounds the wash fountain cylinder and exceeds the height of the latter, wherein the automated analysis device further has a controller, which is configured in such a way that it controls a method with the following steps:
   lowering the pipetting needle such that the pipetting needle tip is introduced into the wash fountain cylinder;
   measuring the fill level of the wash liquid in the wash station with the fill-level sensor; and
   comparing the measured fill level with a first threshold, which corresponds to the height of the wash fountain cylinder.

10. The automated analysis device as claimed in claim 9, further having a screen and/or a loudspeaker and/or a warning lamp.

11. The automated analysis device as claimed in claim 9, wherein the controller is further configured in such a way that an error report is generated if the measured fill level lies above the first threshold.

12. The automated analysis device as claimed in claim 11, wherein the controller is further configured in such a way that the method controlled thereby further comprises the following step:
   stopping the supply of wash liquid into the wash fountain cylinder.

13. The automated analysis device as claimed in claim 11, wherein the controller is further configured in such a way that the error report is indicated on a screen of the automated analysis device in the form of a text message or in the form of a pictogram, or is output in the form of an acoustic signal by a loudspeaker of the automated analysis device or output in the form of a visual signal by a warning lamp of the automated analysis device.

14. The automated analysis device as claimed in claim 9, wherein the controller is further configured in such a way that the method controlled thereby further comprises the following step:
   comparing the measured fill level with a second threshold, which corresponds to a minimum required fill level of the wash liquid in the wash fountain cylinder.

15. The automated analysis device as claimed in claim 14, wherein the controller is further configured in such a way that an error report is generated if the measured fill level lies below the second threshold.

16. The automated analysis device as claimed in claim 9, wherein the automatically displaceable pipetting apparatus comprises a pipetting needle with a capacitive fill-level sensor.

17. The automated analysis device as claimed in claim 9, wherein the measuring comprises:
   measuring a measurement parameter with the fill level sensor as the pipetting needle moves toward the wash liquid until a measured value of the measurement parameter changes; and
   calculating the fill level based on the lowering path of the pipetting needle which ends at a point at which the measured value of the measurement parameter changes.

* * * * *